United States Patent
Hong

(10) Patent No.: US 9,157,871 B2
(45) Date of Patent: Oct. 13, 2015

(54) METHOD AND APPARATUS TO ENHANCE COLLECTION OF PARTICLES IN PARTICULATE MASS MEASUREMENT DEVICE

(75) Inventor: Seung-Ho Hong, Medford, OR (US)

(73) Assignee: Met One Instruments, Inc., Grants Pass, OR (US)

(*) Notice: Subject to any disclaimer, the term of this patent is extended or adjusted under 35 U.S.C. 154(b) by 452 days.

(21) Appl. No.: 13/546,631

(22) Filed: Jul. 11, 2012

(65) Prior Publication Data

US 2014/0013823 A1   Jan. 16, 2014

(51) Int. Cl.
| | |
|---|---|
| *B05B 1/28* | (2006.01) |
| *G01N 23/02* | (2006.01) |
| *G01N 1/22* | (2006.01) |

(52) U.S. Cl.
CPC .............. *G01N 23/02* (2013.01); *G01N 1/2205* (2013.01); *G01N 2001/2223* (2013.01)

(58) Field of Classification Search
CPC .................................... G01N 1/28; B05B 1/28
USPC ........ 73/28.04, 28.05, 863.21, 864.81, 865.5; 250/222.2, 288; 324/71.4; 356/335–343; 96/62; 118/300, 118/313–315, 52; 239/290–293
See application file for complete search history.

(56) References Cited

U.S. PATENT DOCUMENTS

| | | | |
|---|---|---|---|
| 3,711,707 A | 1/1973 | Lilienfeld et al. | |
| 4,506,541 A | 3/1985 | Cunningham | |
| 4,542,644 A | 9/1985 | Claytor et al. | |
| 4,895,034 A | 1/1990 | Poole | |
| 4,954,715 A * | 9/1990 | Zold | 250/461.1 |
| 5,128,539 A | 7/1992 | Rodgers et al. | |
| 5,160,514 A * | 11/1992 | Newbold et al. | 96/8 |
| 5,359,907 A * | 11/1994 | Baker et al. | 73/865.5 |
| 5,571,945 A | 11/1996 | Koutrakis et al. | |
| 5,604,335 A | 2/1997 | Isahaya | |
| 5,682,235 A * | 10/1997 | Igushi | 356/335 |
| 5,808,737 A | 9/1998 | Edens et al. | |
| 5,970,781 A * | 10/1999 | Hiss et al. | 73/28.01 |
| 6,003,389 A | 12/1999 | Flagan et al. | |

(Continued)

FOREIGN PATENT DOCUMENTS

JP   2001343319 A   12/2001

OTHER PUBLICATIONS

S. Seshadri et al., "Use of sheath flow to reduce wall losses in rectangular slot virtual impactors", 2006 Int'l Aerosol Conference, Aerosol Technology Lab, Aug. 13, 2006, 3 pages.

(Continued)

*Primary Examiner* — Hezron E Williams
*Assistant Examiner* — Hoang Nguyen
(74) *Attorney, Agent, or Firm* — Thomas Schneck

(57) ABSTRACT

A particulate mass measuring device of the beta attenuation type featuring a sheath air plenum from which a radial sheath airflow pathway extends which is in fluid communication with an ambient air chamber. The radial sheath airflow from the radial sheath airflow pathway merges with an axial ambient airflow from the ambient air chamber deflecting particulate matter from surfaces of the ambient air chamber thereby increasing the accuracy of particulate mass measurements. The radial sheath airflow is particle free or substantially particle free. In other embodiments, the radial sheath airflow is used to deflect particulate matter in other particulate mass measuring devices, such as those that measure particulate mass in liquid and gas samples.

18 Claims, 2 Drawing Sheets

(56) References Cited

U.S. PATENT DOCUMENTS

| | | | |
|---|---|---|---|
| 6,109,098 | A | 8/2000 | Dukhin et al. |
| 6,230,572 | B1 * | 5/2001 | Pui et al. .................... 73/863.21 |
| 6,454,862 | B1 | 9/2002 | Yoshida et al. |
| 6,473,172 | B1 | 10/2002 | Pelmulder |
| 6,639,671 | B1 | 10/2003 | Liu |
| 6,744,507 | B2 * | 6/2004 | Yamaguchi .................. 356/336 |
| 6,787,763 | B2 | 9/2004 | De La Mora et al. |
| 6,809,314 | B2 | 10/2004 | Yamada et al. |
| 7,111,496 | B1 * | 9/2006 | Lilienfeld et al. ........... 73/28.01 |
| 7,161,143 | B2 | 1/2007 | De La Mora et al. |
| 7,416,902 | B2 | 8/2008 | Pletcher et al. |
| 2006/0169065 | A1 * | 8/2006 | Solomon et al. ........... 73/863.21 |
| 2007/0017673 | A1 | 1/2007 | Hurst et al. |
| 2007/0092976 | A1 * | 4/2007 | Watson et al. ................ 436/181 |
| 2009/0222218 | A1 | 9/2009 | Chamberlin et al. |
| 2009/0252874 | A1 * | 10/2009 | Essien et al. ............. 427/255.25 |
| 2010/0089183 | A1 * | 4/2010 | Solomon .................... 73/863.22 |
| 2010/0142314 | A1 | 6/2010 | Truce et al. |
| 2010/0229657 | A1 | 9/2010 | Weinstein |
| 2010/0330690 | A1 | 12/2010 | Kimoto et al. |
| 2012/0012744 | A1 | 1/2012 | Wang et al. |

OTHER PUBLICATIONS

Printout: Kimoto Data Sheet, "Dichotomous Monitor PM2.5/PM10-2.5/PM10/0BC", PM-712, May 2010, 2 pages.

Operation Manual, "E-BAM Particulate Monitor Operation Manual—E-BAM-9800 Rev L", Met One Instruments, 2008, 5 pages.

E.S. Macias, "Atmospheric Particulate Mass Measurement with Beta Attenuation Mass Monitor", Environmental Science & Technology, vol. 10, No. 9, Sep. 1976, pp. 904-907.

Book: "Aerosol Measurement—Principles, Techniques, and Applications", Wiley-Interscience, 2nd edition, pp. 389-395.

Wm. T. Winberry, Jr. et al., EPA/6251R-96/101a, "Determination of PM10 in ambient air using the andersen continuous beta attenuation monitor", Compendium of Methods for the Determination of Inorganic Compounds, in Ambient Air, Compendium Method 10-1.1, Center of Environmental Research Information, Office of Research and Development, Jun. 1999, pp. 1.1-1 thru 1.1-29.

Printout: J.E. Brockman et al., "Aerodynamic Focusing of Large Particles", 5th Int'l Aerosol Conference, Edinburgh Conference Center, Sep. 12-18, 1998, Sandia National Laboratories, Albuquerque, New Mexico, 12 pages.

* cited by examiner

METHOD AND APPARATUS TO ENHANCE COLLECTION OF PARTICLES IN PARTICULATE MASS MEASUREMENT DEVICE

TECHNICAL FIELD

The field of the invention pertains to particulate mass measurement methods and devices.

BACKGROUND ART

Accurate measurements of toxic pollutants are essential to a proper assessment of air, fluid and gas quality. In particular, ambient air particulate matter less than or equal to 10 microns in size ($PM_{10}$) has been recognized as matter which can be inhaled deeply into the respiratory system and which may cause adverse health effects. The greater the concentration of particulate matter in the ambient air, the greater the risk of health problems caused by the ambient air. Particulate matter measuring devices measure the mass concentration of particulate matter within ambient air, gases or fluids to determine the quality. The measuring devices use different sensing techniques to provide continuous monitoring of particulate mass concentration. Examples of sensing techniques are beta radiation attenuation and optical sensing methods. These measuring devices can provide a warning to a user when detecting a relatively low air quality based upon a relatively large particulate mass concentration within the air.

A particulate measuring device of the beta attenuation type is used to determine a mass concentration of a desired range of sizes of particulate matter through beta attenuation. FIG. 1 depicts a particulate mass measuring device of the beta attenuation type 10 known in the art. The monitor features a nozzle 12 having an ambient airflow chamber 14 with an axial ambient airflow pathway 16 therein. The airflow chamber has a neck 18 with an ambient air inlet 20 and curved surfaces 22 extending from the neck. A beta radiation source housing 24 disposed within the ambient airflow chamber 14 houses a beta radiation source 26 used in the determination of particulate mass concentration. During operation, the ambient air 28 being sampled (or other sample) enters the chamber through the inlet and flows to a filter tape 30 beneath the beta radiation source. Typically, before the ambient air enters the ambient airflow chamber, particles greater than a select size, (e.g. particles greater than 10 microns) are separated from the rest of the sample using impaction separation. Beneath the filter tape 30 is a beta radiation detector 32. The filter tape 30 collects the particulate matter present within the ambient air over time and the remainder of the sample flows out the outlet 34. As the amount of particulate matter collected by the filter tape 30 increases, the particulate matter attenuates the beta radiation emitted from the beta radiation source 26 as detected by the detector (i.e., the beta radiation detector senses less radiation from the beta radiation source). Thus, the attenuation of the beta radiation detected by the beta detector is related to the mass of the particulate matter collected by the filter tape 30 in a specific location. A beta radiation signal produced by the beta radiation attenuation device is used to calculate a mass concentration of particulate matter within a sample over a specified period of time.

With reference to FIG. 2, a problem with the prior art measuring devices is that when ambient air 28 enters the ambient airflow chamber 14, particulate matter 36 from ambient air (in particular, larger diameter or massive particulate matter having a size of 10 microns or less ($PM_{10}$)) may impact and be retained on the surfaces of and/or within the ambient airflow chamber, such as curved or bent surfaces 22. Particulate matter having a size of 2.5 microns or less $PM_{2.5}$ may become stuck also, however, the problem of particulate loss is more pronounced in $PM_{10}$ particulate matter samples. This is because larger particles having greater inertial force are not as influenced by the air sample trajectory as the smaller particles and eventually hit the curved or bent surfaces of or within the nozzle 12 and become stuck. These stuck particles 38 will then not be accounted for when mass measurements are made often resulting in an inaccurate measurement. Further, particles stuck on surfaces of the ambient airflow chamber may accumulate on the ambient airflow chamber surfaces until random, naturally occurring phenomena cause them to dislodge and generate anomalous mass measurements in the ambient air sample.

What is desired is a particulate mass measuring device that provides more accurate mass measurements of particulate matter within a sample.

What is desired is a method for improving the accuracy of particular mass measurements in a particulate mass measuring device.

SUMMARY DISCLOSURE

A particulate mass measurement device comprises, in one embodiment, a beta attenuation mass measurement device featuring a sheath air plenum in fluid communication with an ambient axial airflow chamber. A radial sheath airflow pathway extends into a chamber and merges with the axial ambient airflow pathway to deflect ambient airflow particulate matter from curved or bent surfaces. Thus, particulate matter that may have otherwise impacted and been retained on surfaces of the nozzle is able to continue along the axial pathway to the filter tape to be included in mass measurements thereby increasing the accuracy of the mass measurements and mass concentration measurements within a sample. In one embodiment, the radial sheath airflow pathway merges at a curved surface of the nozzle. Radial sheath airflow is, in one example, substantially free of particulates, and is, in another example, completely free of particulates.

The sheath air plenum and radial sheath airflow pathway may be incorporated into mass measurement devices other than a mass measurement device of the beta attenuation type and may be used for particulate mass measurements in samples other than ambient air, such as liquids and gases.

A method of an embodiment of the present invention comprises providing in a particulate mass measurement device an axial fluid flow within the axial flow pathway of a chamber and merging a radial sheath airflow with the axial fluid flow to deflect ambient air particulate matter from surfaces within the chamber, thereby resulting in more accurate ambient air particulate mass measurements. In one embodiment, the radial sheath airflow merges at a curved surface of the axial airflow chamber. The method may be used to measure particulate matter in a variety of fluid samples including ambient air, liquids and gases.

DETAILED DESCRIPTION

Figure 1:
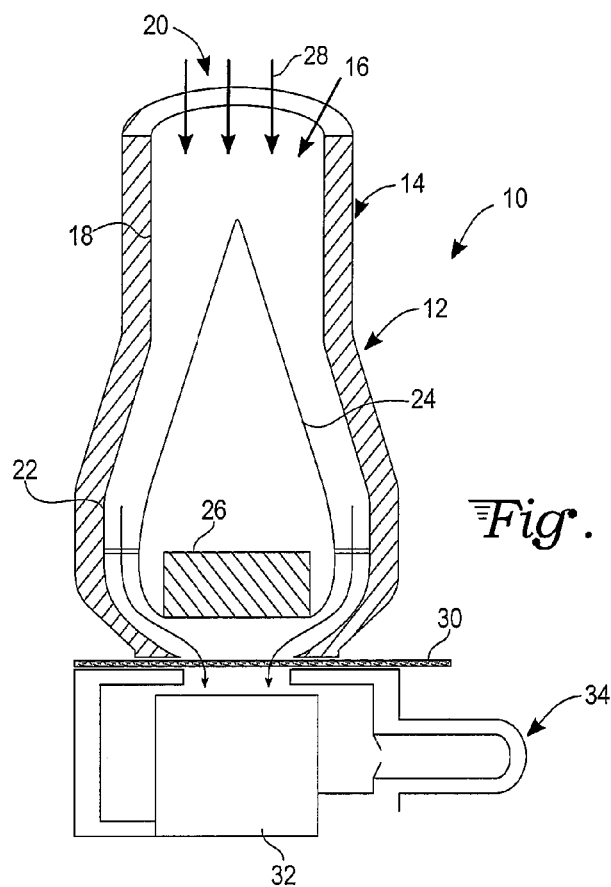
FIG. 1 is a front sectional view of a prior art particulate mass measurement device of the beta attenuation type.
Figure 2:
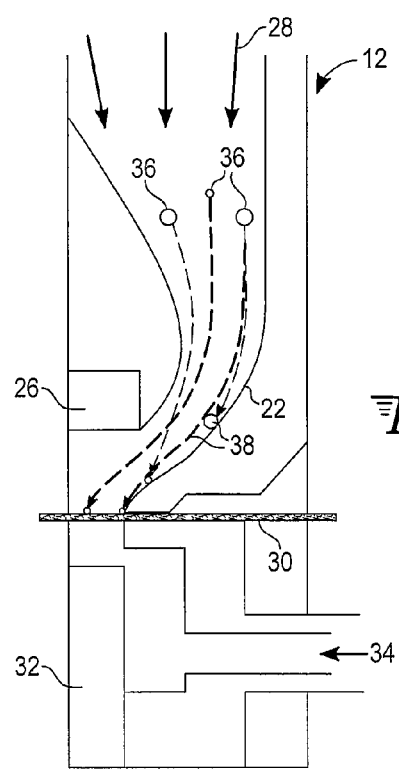
FIG. 2 is a magnified view of a portion of the prior art mass measurement device of claim 1.
Figure 3:
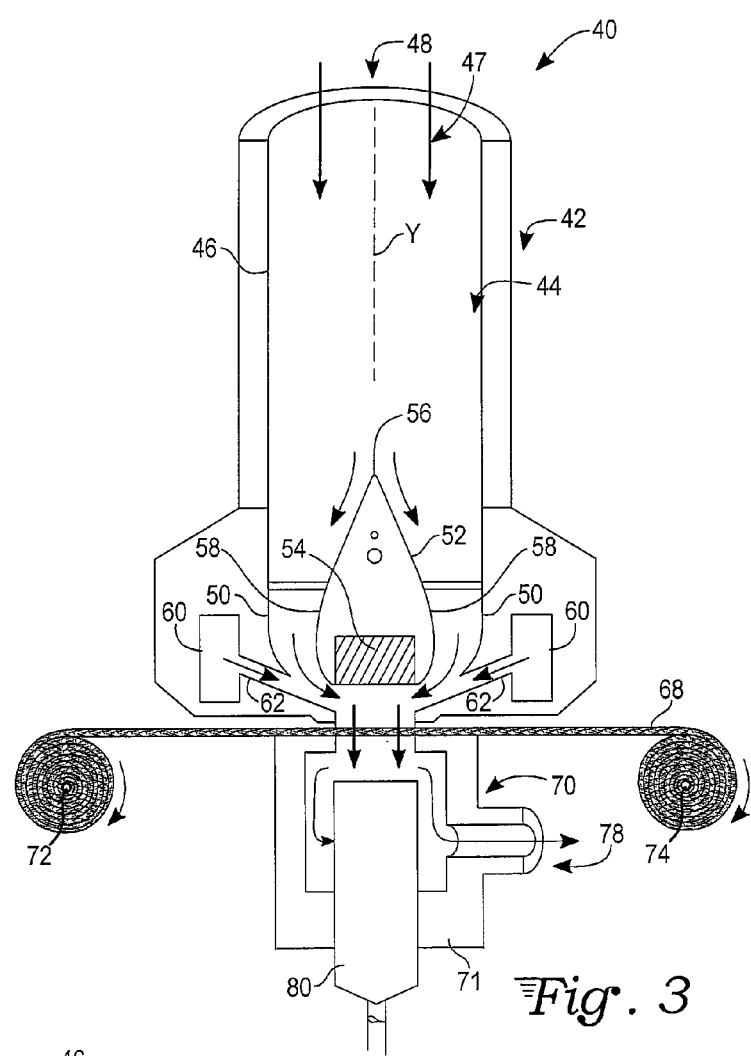
FIG. 3 is a front sectional view of a particulate mass measurement device of the beta attenuation type of an embodiment of the present invention.

With reference to FIG. 3, a particulate mass measurement device embodiment of the present invention is seen. The particulate mass measurement device 40 is of the beta mass attenuation type and includes a nozzle 42 having an ambient airflow chamber 44 with an axial ambient airflow pathway 47 therein. The airflow chamber 44 has a guide pipe or guide neck 46 with an ambient air inlet 48 and curved or bent surfaces 50 extending from the neck 46. A beta radiation source housing 52 is disposed within the ambient air flow chamber 44. A beta radiation source 54 is disposed within the beta source housing 52. The beta radiation source 54 may comprise, for example, carbon-14. The beta source housing 52 which includes, for example a pointed top 56, and annular circumferentially symmetrical sides 58, splits the axial ambient airflow pathway 47. A sheath air plenum 60 is in fluid communication with the ambient airflow chamber 44 and a radial sheath airflow pathway 62 extends from the plenum 60 and merges with the ambient airflow pathway 47. The ambient airflow pathway is, for example, non turbulent. In one example, the radial sheath airflow pathway 62 merges with the axial ambient airflow pathway 47 at curved surface 50 of the chamber. In one example, radial sheath airflow pathway merges at the start of the curved surface 50. The sheath air plenum 60 is, for example, annular and circumferentially symmetrical. The radial sheath airflow pathway 62 is, for example annular and circumferentially symmetrical.

Figure 4:
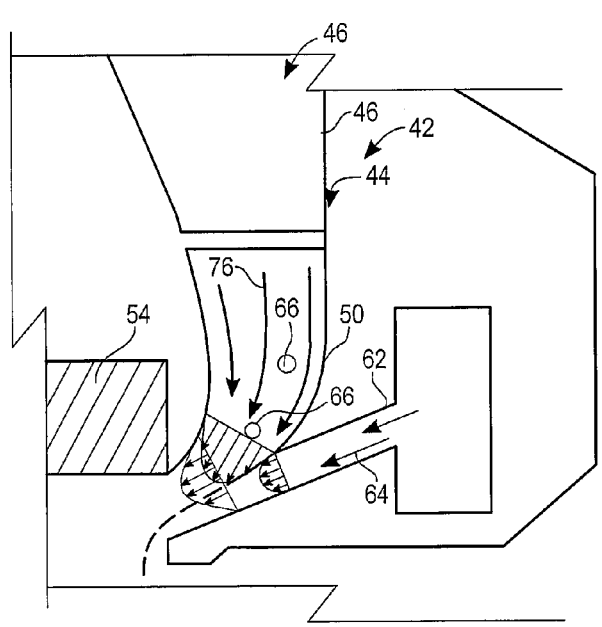
FIG. 4 is a magnified view of a portion of the particulate mass measurement device of FIG. 3.

Referring to FIG. 4, radial sheath airflow 64 from within the radial sheath airflow pathway 62 deflects ambient air particulate matter 66 from the curved chamber wall surfaces 50 and/or from other surfaces in the chamber 44 as it merges with axial ambient airflow 76. The radial sheath air stored within the radial sheath plenum 60 and the radial sheath airflow 64 from the radial sheath plenum 60 are, in one example, substantially particle free, and, in another example, particle free. It is desired that the radial sheath air is particle free or substantially particle free so that no or few particles from the radial sheath air are included in the particle count of the sample.

Referring back to FIG. 3, the nozzle 42 further includes filter tape 68 separating a detection chamber 70 from the ambient airflow chamber 44. In one example, the filter tape is a glass fiber filter tape. It may be clamped in between the nozzle 44 and the detection chamber 70. The filter tape 68 is, for example a reel, wound on a first spindle 72 and a second spindle 74 so that it may be advanced after a certain sampling time.

Typically larger particles in ambient air to be sampled, for example particles greater that 10 microns in diameter, are separated from the sample before particulate mass in the sample is determined. This separation may occur through impaction separation using impaction plates (not shown). This is because these larger particles are not typically inhaled deeply into the respiratory system as are particles 10 microns or less in diameter and therefore are not as likely to cause adverse health effects. In another example, particles larger than 2.5 microns are separated from the ambient air sample before particulate mass concentration is determined. The remaining ambient air sample having for example, particles that are 10 microns or smaller, traverses the inlet 48 of the ambient airflow chamber 44 and travels along an axis y of the chamber 44.

More precisely, the apparatus captures particles for measurement with a PM-10 standard or better (e.g., PM-2.5). This means that for PM-10, particles with a diameter of 10 microns have a 50% capture rate, increasingly larger particles have a somewhat lower capture rate (e.g., 30% for 11-micron particles, 10% for 12-micron particles, etc.), increasingly smaller particles have high capture rates than 50% (e.g., 70% for 9-micron particles, 90% for 8-micron particles, etc.) Likewise, for PM-2.5, the 50% capture rate would be for 2.5 micron particles.

In a method of the present invention, radial sheath airflow 64 merges with the axial ambient airflow 76, as seen in FIG. 4, to deflect particulate matter 66 from surfaces of the airflow chamber 44, such as curved surface 50, so that the particulate matter may be included in mass measurements, thereby resulting in more accurate ambient air particulate mass measurements. The method may be used to measure particulate matter in a variety of fluid samples including ambient air, liquids and gases.

Referring to FIGS. 3 and 4, particulate matter 66 then travels with the axial ambient airflow 76 and is deposited on the filter tape 68 while the remaining ambient air sample passes through to the detection chamber 70 to the outlet 78. A low level of beta radiation is emitted from the beta radiation source and passes through the filter tape 68 and deposited particles (not shown). The increase of particles collected on the filter tape 68 causes a lower beta-ray measurement in the detection chamber 70. Beta radiation detector 80 within detector housing 71 of detection chamber 70 is, for example, a photomultiplier. Particulate mass measuring devices of the beta attenuation type exhibit an attenuation characteristic as a function of the mass per unit area collected by the filter tape 68. The increase of particles collected on the filter tape 68 causes a lower beta-ray measurement in the detection chamber 70. By measuring the accumulated mass of particles on the filter tape 68 and the volumetric flow rate of ambient air, the particulate mass measuring device 40 can calculate the mass concentration of particles in the air or other sample.

Particulate matter of the sample that may have otherwise impacted and been retained on surfaces of the nozzle 42 is able to continue along the axial pathway to the filter tape 68 to be included in mass measurements thus increasing the accuracy of the mass measurements and mass concentration measurements within a sample. An additional advantage is that the presence of the radial sheath airflow in the chamber 44 reduces maintenance costs by preventing particles 60 from building up on internal chamber surfaces, such as surfaces 50.

The sheath air plenum and radial sheath airflow pathway may be incorporated into mass measurement devices other than a mass measurement device of the beta attenuation type and may be used for particulate mass measurements in samples other than ambient air, such as liquids and gases.

What is claimed is:

1. A particulate mass measurement apparatus of a beta mass attenuation type comprising:
a nozzle having an ambient airflow chamber with an axial ambient airflow pathway therein, the airflow chamber having a neck with an ambient air inlet and curved surfaces in the airflow direction extending from the neck;
a beta radiation source housing disposed within the ambient air flow chamber and a beta radiation source disposed within the beta source housing, the beta source housing having a curved surface in the airflow direction splitting the axial ambient airflow pathway;
a sheath air plenum in fluid communication with the ambient airflow chamber and a radial sheath airflow pathway extending from the plenum and merging with the ambient airflow pathway, wherein radial sheath airflow from within the radial sheath airflow pathway is substantially particle free air that merges with the ambient airflow between curved surfaces of the airflow chamber and the beta source housing guiding the ambient airflow thereby deflecting ambient air including ambient air particulate matter from the curved chamber wall surfaces;

a filter tape disposed beneath the beta source;

a beta radiation detector disposed beneath the filter tape; and an outlet.

2. The apparatus of claim 1, wherein the plenum is annular.

3. The apparatus of claim 2, wherein the plenum is circumferentially symmetric.

4. The apparatus of claim 1, wherein the radial sheath airflow pathway is annular.

5. The apparatus of claim 4, wherein the radial sheath airflow pathway is circumferentially symmetric.

6. The apparatus of claim 1, wherein the beta housing has a pointed top and is circumferentially symmetrical.

7. A particulate mass measurement apparatus of a beta attenuation type comprising a nozzle having an ambient airflow chamber with walls having a curved surface in the airflow direction and an axial ambient airflow pathway therein, a beta radiation source housing having a curved surface in the airflow direction disposed within the ambient airflow chamber, a beta radiation source disposed within the beta source housing, a filter tape disposed beneath the beta source, and a detector disposed beneath the filter tape, wherein the improvement comprises:

a sheath air plenum holding substantially particle free air in fluid communication with the ambient airflow chamber with walls and a radial sheath airflow pathway extending from the plenum and merging with the axial ambient airflow pathway, between curved surfaces of the airflow chamber and the beta source housing wherein the radial sheath airflow merges with the axial ambient airflow and deflects ambient air including ambient air particulate matter from the chamber walls.

8. The apparatus of claim 7, wherein the sheath air plenums store substantially particle free air.

9. The apparatus of claim 7, wherein the plenum is annular.

10. The apparatus of claim 9, wherein the plenum is circumferentially symmetrical.

11. The apparatus of claim 7, wherein the radial sheath airflow pathway is annular.

12. The apparatus of claim 11, wherein the radial sheath airflow pathway is circumferentially symmetrical.

13. A method for improving the accuracy of particulate mass measurements in a particulate mass measurement device having an airflow chamber with an axial flow pathway therein and curved surfaces in the flow pathway direction on which particulate matter from a fluid flow may impact, with a beta source curved wall housing in the chamber, the method comprising:

providing an axial fluid flow within the axial flow pathway of the chamber; and merging a substantially particle free radial sheath airflow between curved surfaces of the airflow chamber and the beta source curved wall housing with the axial fluid flow to deflect ambient air including ambient air particulate matter from surfaces within the chamber, thereby resulting in more accurate ambient air particulate mass measurements.

14. The method of claim 13 wherein the radial sheath airflow is substantially particle free.

15. The method of claim 13, wherein the axial ambient airflow is non turbulent.

16. The method of claim 13, wherein ambient air particulate matter size is 10 microns or less.

17. The method of claim 13, wherein the fluid flow is ambient air.

18. The method of claim 13, wherein the fluid flow is a liquid.

* * * * *